United States Patent [19]

Jaquet

[11] 4,365,624

[45] Dec. 28, 1982

[54] EXTERNAL BONE-ANCHORING ELEMENT

[75] Inventor: Henri Jaquet, Le Grand Saconnex, Switzerland

[73] Assignee: Jaquet Orthopedie SA, Switzerland

[21] Appl. No.: 107,546

[22] Filed: Dec. 27, 1979

[30] Foreign Application Priority Data

Jan. 16, 1979 [CH] Switzerland .......................... 386/79

[51] Int. Cl.³ .............................................. A61F 5/04
[52] U.S. Cl. ................................... 128/92 A; 128/82; 128/84 B
[58] Field of Search .............. 128/92 A, 92 R, 82–84, 128/84 B, 84 C, 92 B, 92 C

[56] References Cited

U.S. PATENT DOCUMENTS

| 3,196,875 | 7/1965 | Pfeiffer . | |
| 4,185,623 | 1/1980 | Volkov et al. | 128/92 A X |
| 4,271,832 | 6/1981 | Evans et al. | 128/92 A |

FOREIGN PATENT DOCUMENTS

| 606579 | 5/1978 | U.S.S.R. | 128/92 A |
| 667205 | 6/1979 | U.S.S.R. | 128/92 A |

Primary Examiner—Stephen C. Pellegrino
Attorney, Agent, or Firm—Ostrolenk, Faber, Gerb & Soffen

[57] ABSTRACT

Broken bones are externally anchored by various embodiments of the disclosed invention. In each of the embodiments one or more arcuate members pass around the bone to be anchored. Pins extend from the arcuate members to and may also transfix the bone to be anchored. In some embodiments, there are a plurality of arcuate members. In some of the embodiments, the arcuate members encircle the bone. Various auxiliary support pieces are attached on the arcuate members. Some of these auxiliary support pieces help anchor the arcuate members. Other of these auxiliary pieces provide additional supports for additional bone supporting pins. The pins may be held on swivel joints so that the pins may be swiveled for properly engaging a bone. The arcuate members are attached to support supports which enable the anchoring arcuate members to extend to other supporting elements.

39 Claims, 24 Drawing Figures

EXTERNAL BONE-ANCHORING ELEMENT

BACKGROUND OF THE INVENTION

The invention relates to an external bone-anchoring element.

External anchoring of bones is an old surgical technique which was first used a century ago. Its application has for a long time been limited to complicated fractures in traumatology and consequently in orthopedics, i.e. the secondary treatment of fractures, infections slow knitting of the bones, pseudarthroses, difficult bone-settings, etc.

External anchoring is used more particularly for long bones such as the femur, the tibia, the humerus, the radius, the cubitus and, in particular, the bones in the leg.

It is desirable to be able to extend the use of the external anchoring means to the pelvic basin, the clavicle, to joints such as the knee, elbow and shoulder, and to the skull for the treatment of the cervical and lumbar vertebrae, etc.

It is also desirable to manufacture small anchoring means which can be used on small bones, such as the metatarsals and the metacarpals, and in maxillofacial surgery as well as in experimental surgery on small animals.

External bone-anchoring elements enable two kinds of bone-anchoring to be carried out:
- transfixing anchoring, wherein the pins extend from one side of the limb to the other, and
- non-transfixing anchoring, wherein the pins are introduced into the bone without completely transversing it. Transfixing anchoring, which is mostly used on the leg, is more rigid than non-transfixing anchorage.

Fitted at both sides of the leg are two rods or frames which are anchored on two groups of pins disposed on either side of the fracture. The two frames or the two rods are interconnected by a brace which is as stable as possible and which may comprise sliding rods or bars, the length of which can be increased or reduced.

External anchoring means made up of rings are also in existence. Such anchoring means are described for example in Swiss Pat. Nos. 579,385 and 596,826 which relate to the use of external anchoring means using the "Russian" method. The anchoring means described in these two patents are based solely on the use of circles. These are therefore the circles which form the frames and the braces. These circles can be single or double, i.e. they may surround the bone. It is thought that the single circle will be mostly used if there are two groups of parallel pins on each bone fragment. In certain cases, a different problem arises. If the bone fragment is very short, i.e. near a joint, and the fragment is not long enough to allow two or three parallel pins to be secured, use may be made of another method, such as that described by the Russians, in which method a very short bone fragment can be anchored by providing a circular support on which are secured smooth transfixing intersecting pins (see Swiss Pat. No. 579,385). This patent discloses a device for interconnecting the various rings. But this device is very complicated in its manipulation and it, therefore, does not permit the fracture to be readily set.

Another manufacturer, Kronner, uses a plastic, circular arrangement on which parallel transfixing pins are fitted. This device is also different to use since the pins are offset in relation to the circle. Setting is rendered easier, since the connecting bars are mounted on swivel joints. However, based upon tests that have been performed, the inventor hereof, the immobilizing system using swivel-joints may permit sliding after setting.

All these systems have one point in common, i.e. that of enabling the bone fragments to be moved away or towards each other as required (retraction of compression).

As a general rule, anchoring means based solely on the use of circles can be extended to apply to the clavicle only with difficulty.

SUMMARY OF THE INVENTION

The present invention seeks to obviate the above described disadvantages and to provide an external bone anchoring element which can be used in combination with existing frames and braces, so that the uses of the anchoring device can thus be extended.

In accordance with a first aspect of the invention, there is provided an external bone-anchoring element comprising at least one arcuate member of polygonal cross-section and support pieces adapted to enable pins or wires, which retain at least one piece of bone, and/or rods, to be secured on the arcuate member.

Assembly pieces may be provided for securing the ends of the arcuate member to the external anchoring means of which the member is a component part.

In one embodiment of the invention, the support pieces and/or the assembly pieces comprise jaws having internal recesses adapted to complement at least a portion of the periphery of the arc so as to be capable of being pressed on to and immobilized on the arc without being able to rotate about it.

Each assembly piece and/or each support piece has a bore into which the rod, pin or wire is introduced. The bore may be provided with a sleeve or lining adapted to match the diameter of the wires and pins to the bore of the piece. The bore may be so disposed that its axis extends radially of the arc when the piece is secured thereto, or in such manner that its axis is perpendicular to the plane of the arc when the piece is secured.

The assembly piece may have a part pivoting about a clamping screw and relative to the piece as a whole. The pivoting part comprises the bore, and the pivoting part may be formed by a clamp which comprises a bore and a slot.

The invention also seeks to provide an external bone-anchoring means comprising the anchoring element in the form of at least one arcuate portion.

In accordance with a second aspect of the invention there is provided an external bone-anchoring means, comprising two groups of at least two pins each retaining a bone portion. The two groups of one or more pins is interconnected by a brace and at least one arcuate member connected to the brace adjacent a group of pins.

At least the pins of one group may be anchored at each of their ends in a clamping device, with the two clamping devices being interconnected by an arcuate portion.

At least the pins of one group may be secured in a cruciform arrangement to at least one semi-circle.

In a preferred embodiment, additional pins designed to hold additional bone fragments in position are secured to the circle with the aid of adequate means adapted to position the additional fragments laterally in relation to the circle.

The preferred cross-sectional shape of the arc is triangular. However, it could be square or of general polygonal shape. For practical reasons, the triangular cross-section is preferred because of its rigidity and the possibility of securing the support and assembly pieces in a simple manner, which enables a large number of different forms of assembly to be used.

In order that the invention may be better understood, several embodiments thereof will now be described by way of example only and with reference to the accompanying drawings.

BRIEF DESCRIPTION OF THE DRAWINGS

FIG. 14 illustrates a front view of an arrangement comprising two quarter-circles held in position by an intermediate piece, the upper portion of which has the same cross-section as that of the quarter-circles;

FIG. 17 is a transverse section through an end clamping piece for a ring, on line XVII—XVII of FIG. 14, wherein the clamping piece is a modified form of the corresponding pieces shown in FIGS. 3 and 4 and wherein it is designed for use with the quarter-circles or semi-circles of the type illustrated in FIGS. 15 and 16;

FIG. 8 is a section along line XVIII—XVIII of FIG. 14;

FIG. 19 is a cross-section through a swivel-joint which carries a pin and which is secured to a quarter-circle, this view being shown along line XIX—XIX of FIG. 14;

DESCRIPTION OF THE PREFERRED EMBODIMENTS

Figure 1:
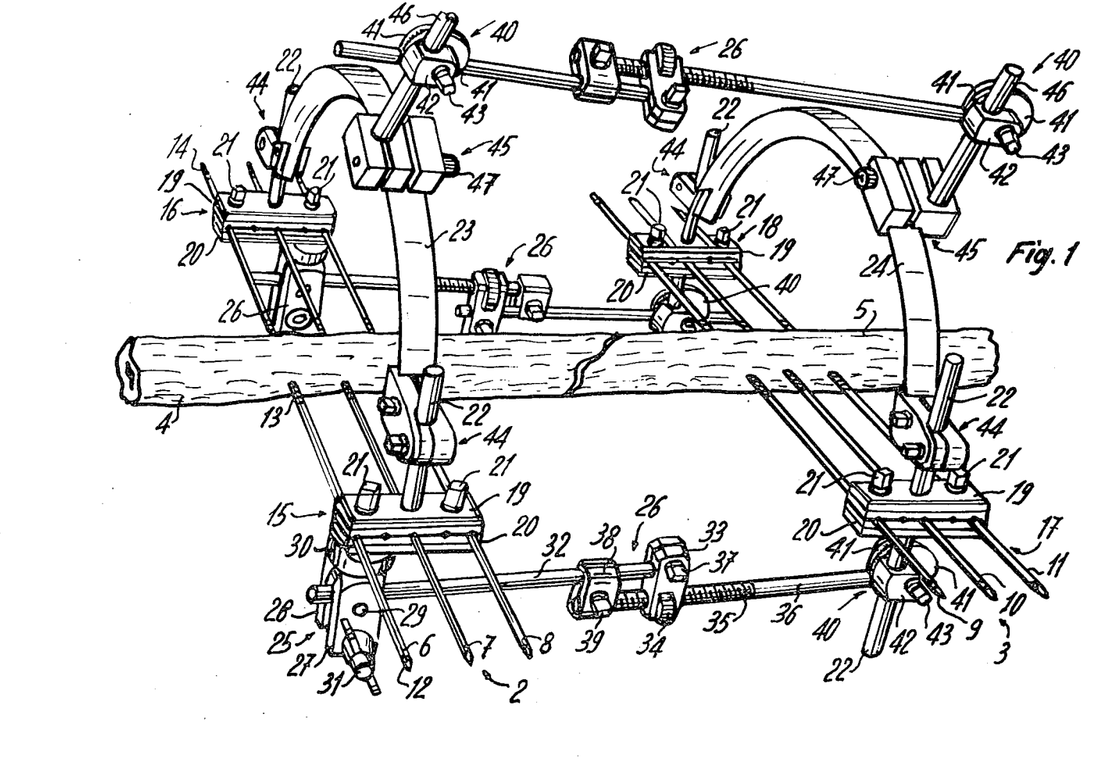
FIG. 1 is a perspective view of an external bone anchoring means comprising two groups of three transfixing pins each, held in position by a frame, an element in the form of a semi-circle being mounted on each group of pins, and bars for joining up the assembly are also shown.

The external bone-anchoring means illustrated in FIG. 1 comprises two groups of pins 2 and 3 designed to hold and retain relatively to each other two bone fragments 4 and 5, respectively. Each of the groups of pins 2 and 3 comprises, respectively, three pins 6, 7, 8 and 9, 10, 11, which pass completely through the bone fragments that they are to hold in position. The pins 6–11 are called transfixing pins. Each has at one of its ends a point 12, as illustrated in the case of the pin 6, and a median threaded portion 13, and each has at its other end a head 14 of square cross-section which enables each pin to be screwed into a bone with the aid of a tool, not illustrated.

The pins 6, 7, 8 of group 2 and the pins 9, 10, 11 of group 3 are each retained at their ends by anchoring clamps 15, 16 and 17, 18, respectively. Each of the clamps 15 to 18 comprises two jaws 19, 20 having on their inner adjacent surfaces appropriate grooves for receiving the pins 6 to 11. The jaws 19 and 20 forming each clamp are pressed against each other by means of two square-headed screws 21. The jaws 19 of the clamps 15 and 16 and the jaws 19 and 20 of the clamps 17 and 18 are integral, respectively, with a rod 22 disposed vertically of the plane of each clamp. The upper portions of the rods 22 of the jaws 19 of the clamps 15 to 18 enable semi-circles 23 and 24, respectively, to be fitted. The jaws 20 of the clamps 15 and 16 are integral with a respective swivel-joint 25 designed to receive the stem of a respective slide bar 26. The swivel-joint 25 comprises two lateral pieces 27 and 28 permitting the gripping of a central circular piece, not illustrated, that is adapted to turn about a spindle 29 and into which a stem of the slide bar 26 is introduced. The circular central piece may turn about the spindle 29, and the two lateral pieces 27 and 28 are held in a circular recess, not illustrated, located within a collar 30 integral with the jaw 20. The clamping action of the swivel-joint is achieved by means of a wing-nut 31.

The slide bars 26 comprises a stem 32 at the end of which is secured a piece 33 having a small roller 34 which meshes with a screw-threaded part 35 of a second stem 36. The piece 33 is clamped to the end of the stem 32 by means of a square-headed screw 37. Provided at the end of the screw-threaded part 35 of the stem 36 is a sliding piece 38 designed to slide on the stem 32 when the roller 34 is turned in one or other direction so as to lengthen or shorten the slide bar 26. The sliding piece 38 may also be immobilized on the stem 32 by means of a square-handed screw 39. As already mentioned above, the slide bars 26, located below the plane defined by the pins 6 to 11, are secured, on the one hand, in the swivel-joints 25 integral with the lower jaws 20 of the clamps 15 and 16 and, on the other hand, in toothed swivel-joints 40 secured to the stems 22 of the jaws 20 of the clamps 17 and 18. The toothed swivel-joints 40 each comprises two discs 41 which are applied to each other and the adjacent surfaces of which are toothed. The outer surfaces of the discs comprise parts 42 designed to receive and retain by friction stems, for example the stems 36 of the slide bars 26 on the one hand, and on the other hand, the stems 22 of the lower jaws of the clamps 17 and 18. The toothed swivel-joints 40 are immobilized by means of a square-headed screw 43.

The semi-circles 23 and 24 are each secured to the stems 22 of the upper jaws 19 of the clamps 15, 16, 17 and 18 with the aid of assembly pieces 44 which enable the ends of the semi-circles 23 and 24 and the stem 22 to be gripped by friction. The assembly pieces 44 will be described in detail hereinafter by reference to FIGS. 3 and 4. After the semi-circles 23 and 24 have been positioned and immobilized on the stems 22 of the clamps 15 to 18 with the aid of the pieces 44, support pieces 25 in which the rods 46 are clamped are secured to said semi-circles. The pieces 45 are support pieces adapted to be secured on the semi-circles 23 and 24 and to retain the rod 46 by friction and radially of the semi-circle, by means of a single screw 47. The pieces 45 will now be described in detail with reference to FIGS. 7 and 8. Secured to the rods 46 are toothed swivel-joints 40 identical to those described above, and a slide bar 26 is placed between the two swivel-joints 40 secured to the rod 46.

In the embodiment of the external anchoring means which has just been described, the two groups 2 and 3 of pins 6, 7, 8 and 9, 10, 11, respectively, retain two bone fragments which can be held in any required position relative to each other. The two slide bars 26 located below the plane defined by the groups 2 and 3 of pins form, together with the swivel-joints 25, the toothed swivel-joints 40 and the rods 22, a lower fitting. The two semi-circles 23, 24, the assembly pieces 44 and 45 and the swivel-joints 40 mounted on the rods 46 and used for mounting the upper slide bar constitute the upper fitting of the external anchoring means of FIG. 1.

The external bone-anchoring means 1 illustrated in FIG. 1 is positioned in the following way:

The two groups 2 and 3 of pins 6, 7, 8 and 9, 10, 11, respectively, are placed in position with the aid of a template or guide and a brace, not illustrated. Since a template is used, the pins of each of the two groups 2 and 3 are perfectly parallel with the other pins of the group and the pins are equidistantly spaced so that they can be introduced and clamped without difficulty between the jaws 19 and 20 of the clamps 15, 16, 17 and 18. The next step is to position the lower fitting formed by the assembly comprising the two slide bars 26 and the swivel-joints 25 and 40, and the upper fitting comprising the semi-circles 23 and 24, the pieces 44 and 45, the rods 46, the swivel-joints 40 and the third slide-bar 26. The two pieces of bone 4 and 5 can be positioned as required by suitably selecting the positions of the swivel-joints 25 and 40 before immobilization. On the other hand, it is possible to move the pieces of bone away from or towards each other by lengthening or shortening the slide-bars 26 by turning the rollers 34 on the bars in the required direction. The presence of the semi-circles 23 and 24 impart very great rigidity to the system.

Figure 2:
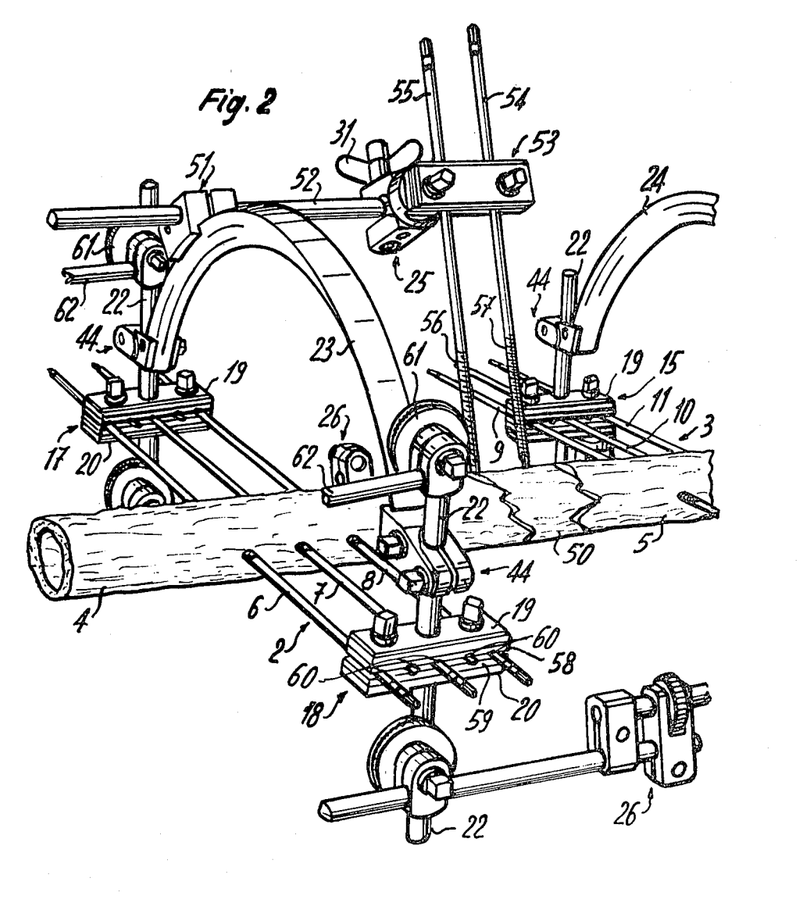
FIG. 2 is a perspective view of a modified form of the anchoring means of FIG. 1, wherein the semi-circles are used for supporting anchoring members carrying pins.

In connection with the variant illustrated in FIG. 2, three bone fragments are to be positioned relatively to each other instead of the two fragments 4 and 5. An additional fragment 50 is placed between the two fragments 4 and 5. As shown in FIG. 2 one of the arcs, i.e. the arc 23, is to carry a support element, described below, which enables the bone fragment 50 to be held in position. In this variant the two groups 2 and 3 of three pins 6, 7, 8 and 9, 10, 11, respectively, are again held in position between the jaws 19 and 20 of the clamps 15, 16, 17 and 18. The rods 22 of the lower jaws 20 of the clamps 17 and 18, as in the FIG. 1 embodiment, support toothed swivel-joints 40, and the lower jaws 20 of the clamps 15 and 16 carry joints with wing-nuts 25, and sliding bars 26 are placed between the joints 25 and 40 to form the lower fitting. The rods 22 of the upper jaws 19 of the clamps 15, 16, 17 and 18 carry assembly pieces 44 which enable the semi-circles 23 and 24 to be held in position and clamped. The assembly pieces are identical to those of FIG. 1 and will be described in detail hereinafter by reference to FIGS. 3 and 4. Placed on the semi-circle 23 is a support piece 51 which enables a rod 52 to be secured parallel to the axis of the bone fragments 4 and 5 or perpendicular to the plane of the semi-circles 23 and 24. The piece 51 will be described in detail hereinafter by reference to FIGS. 5 and 6. Secured to the rod 52 is a swivel-joint 25 with its clamping wing-nut integral with an anchoring clamp 53 similar to the clamps 15 to 18. Held in the clamp 53 are two pin-halves 54 and 55, the screw-threaded ends 56 and 57, respectively, of which are screwed into the bone fragment 50 which is to be positioned between the fragments 4 and 5. As in the case of the pins 6 to 11, the pin-halves 54 and 55 each have, at that end remote from that screwed into the bone fragment 50, a square-section head which enables the pin to be engaged by a wrench for screwing it on to a bone. As illustrated in FIGS. 1 and 2, the pins 54 and 55 are shorter than the pins 6 to 11 which extend completely through the bone. Their screw-thread is provided at one of their ends since they are not intended to extend right through the bone. On the other hand, the pins 6 to 11 in the embodiments shown in FIGS. 1 and 2 are transfixing pins and have a screw-threaded portion at their median zone where they are to be retained in the bone fragments 4 and 5. In the variant shown in FIG. 2, it will be seen that the jaws of the clamps 15 to 18, as in the case of the clamp 53, have (see the clamp 18 in FIG. 2) lower linings 58 and 59, the adjacent surfaces of which are provided with grooves 60 designed to accommodate the pins. As illustrated in the case of the clamp 18 (FIG. 2), five pairs of corresponding grooves 60 are provided. It is thus possible to retain one to five pins in each clamp.

In the FIG. 2 variant, the ends of the rods of the upper jaws 19 carry clamps 17 and 18 of toothed swivel-joints 61, supporting rods 62 which enable the upper frame of the external anchoring means to be extended towards the left. It will be possible to secure, on these rods 62, any additional retaining means considered useful, for example, a pin-half, not illustrated, similar to the halves 54 or 55 and serving to reinforce the anchoring of the fragment 4 at the left and thus to avoid any flexure if force is applied to this bone fragment. An additional pin of this kind could also be secured to the semi-circle 23 by means of a support piece 51, a rod 52 and a clamp 53 all similar to the elements illustrated in FIG. 2, and all extending to the left.

The advantage provided by the arc 23 and the mounting of the elements 51 to 55 or any other arrangement of this type based on an arc resides mainly in the fact that the assembly can be positioned at any point along the arc. The fragment 50 that it supports would then be positioned with precision and without difficulty relatively to the two other bone fragments 4 and 5. On the other hand, since the arc 23 is of triangular cross-section, the rod 52 can be very firmly anchored with the aid of the support piece 51 and will not become displaced. It will also be observed that there remains, on the arc 23 as well as on the arc 24, all the space necessary for providing other assemblies, for example, for providing means for increasing the stability of the anchoring means as a whole, or for reinforcing the anchoring of a bone fragment in relation to the arc.

Figure 3:
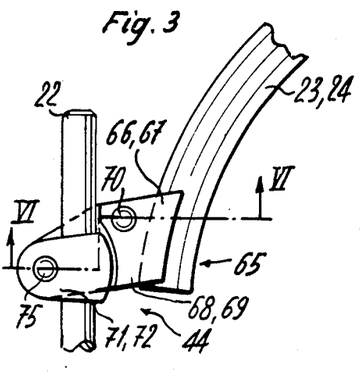
FIG. 3 is a side view showing a clamping piece designed to connect the end of an arcuate part to a rod.
Figure 4:
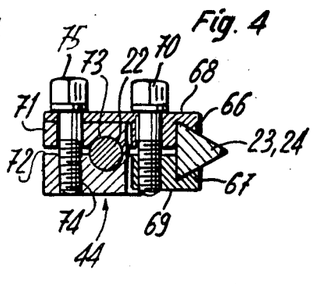
FIG. 4 is a section along line VI—VI of FIG. 3.

As shown in FIGS. 3 and 4, the pieces for fitting the arcs 23 and 24 on the rods 22 enable complete stability to be established between the arc and the rest of the external anchoring means. The end 65 of each of the arcs 23 and 24 of triangular cross-section is held between two oppositely disposed part-circular grooves 66 and 67, the curvature of which corresponds to that of the arcs 23 and 24 and which are formed in two shells 68 and 69 adapted to be pressed against the arcs 23 and 24 by means of a square-headed screw 70. The shell 68 is extended sideways towards the exterior in relation to the end of the arcs 23 and 24 so as to receive a clamping element 71 having a bore 73 and a slot 72. The bore 73 is provided for receiving the rod 22. The screw 75 extends through the shell 68 as well as the clamping element 71. The screw-threaded part 74 permits immobilization of the rod 22 as well as the clamping element 71 with the shell 68. As shown in FIGS. 3 and 4, the clamping element 71 and the rod 22 can pivot about the axis of the screw 75 until the latter is tightened. The assembly piece 44, which has been described by reference to FIGS. 3 and 4, is positioned with the arc in the manner described below:

The square-headed screw 70 is loosened to some extent and the two shells 68 and 69 are moved away from each other. The screw 75 is also loosened to some extent to release the clamp element 71 which opens the slot 72 and this enables the rod 22 to be introduced into the bore 73. The end of the arc 23 or 24 is introduced into the grooves 66 and 67 and the screw 70 is tightened. This causes the two shells 68 and 69 to be immobilized on the ends of the arc. The rod 22 is then introduced into the bore 73 of the clamp element 71, and the assembly is placed at the required point on the rod 22. Since the clamp element 71 can pivot about the axis of the screw 75, fitting on to the rod 22 will be facilitated when the piece 44 is in position on the rod, and when the screw is blocked and the assembly comprising the rod 22, the assembly piece 44 and the arcs 23 and 24 become rigid. If necessary, it is possible first to place the rod 22 in the bore 73 of the clamp element 71. After that, the end 65 of the arc 23 or 24 is brought into the grooves 66 and 67 in the shells 68 and 69. When all these parts are in position, the screws 70 and 75 are tightened.

Figure 5:
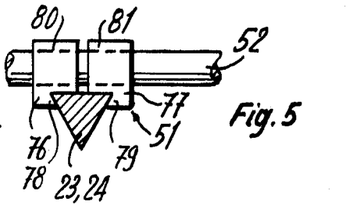
FIG. 5 is a front view showing a lateral anchoring member on a circle, of the type illustrated in FIG. 2.
Figure 6:
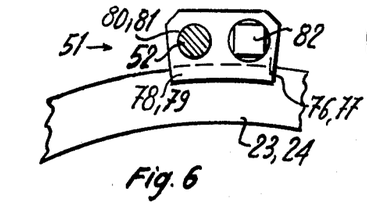
FIG. 6 is a side view of the FIG. 5 anchoring member.

As already mentioned above, the support piece 51, illustrated in detail in FIGS. 5 and 6, enables a rod 52 to be secured perpendicularly to the plane of the arcs 23 or 24 on which it is positioned. The piece 51 comprises two clamping devices 76 and 77 having two grooves 78 and 79 suitable for gripping the triangular cross-section of the arcs 23 and 24. As shown in FIG. 6, the grooves 78 and 79 have the same curvature as the arcs 23 and 24. Each clamping device 76 and 77 is provided at one of its sides with a bore 80 and 81, respectively. The axes of these bores are in alignment when the clamping devices are placed opposite each other. At their other sides, the clamping devices 76 and 77 are interconnected by a square-headed screw 82. The rod 52 is introduced into the bores 80 and 81 of the clamping devices 76 and 77, respectively, which in turn are placed on the arcs 23 and 24. It is only required to tighten the screw 82 to immobilize the clamping devices 76 and 77 on the arcs 23 and 24 and, at the same time, to immobilize the rod 52 by flexion.

The support piece 51, just described by reference to FIGS. 5 and 6, permits the fixing, at any point along the periphery of the arcs 23 or 24, a rod 52 which extends perpendicularly from one or both sides of the plane of the arc. This rod can be used for supporting any device for retaining a fragment of bone or for any device for reinforcing the system as a whole or a part of the external anchoring means of which it is a component part. As already stated, the positioning of the rod 52 along the arcs 23 or 24 is not limited to predetermined points. Thus, the rod can be positioned with precision along the entire arc.

Figure 7:
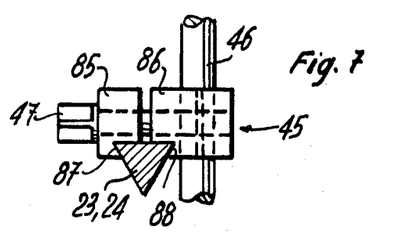
FIG. 7 is a front view showing a radial anchoring member on an arc, of the type illustrated in FIG. 1.
Figure 8:
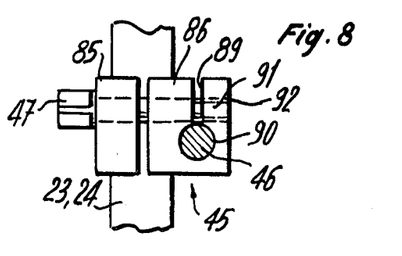
FIG. 8 is a plan view of the anchoring member of FIG. 7.

As already mentioned in connection with the FIG. 1 embodiment, the support piece 45 illustrated in FIGS. 7 and 8 enables a rod to be positioned radially outwardly of the arcs 23 and 24. The piece 45 comprises two clamping devices 85 and 86 each having at its lower part a respective groove 87 and 88, which grooves are adapted to together grip the arcs 23 and 24. The grooves 87 and 88 have a curvature identical to that of the arcs 23 and 24. The clamping device 86 has a slot 89 which delimits two clamping tabs and the slot 89 runs into a bore 90 designed to receive the rod 46. The two clamping devices 75 and 86 are interconnected by the square-headed screw 47, the screw-threaded portion 91 of which meshes with a screw-threaded portion 92 formed in the outer clamping lug of the element 86. It can be seen from FIG. 8 that tightening of the screw 47 immobilizes, on the one hand, the two clamping elements 85 and 86 on the arc, and on the other hand, the rod 46 in the bore 90. As in the case of the support piece 51 shown in FIGS. 5 and 6, the piece 45, illustrated in FIGS. 7 and 8 and just described, can be placed at any point along the arcs 23 and 24. The rod 46 that the piece 45 is to grip can be used either as a support for any means for retaining a bone fragment, or as a support for increasing the stability of the external anchoring means of which it is a component part.

Figure 9:
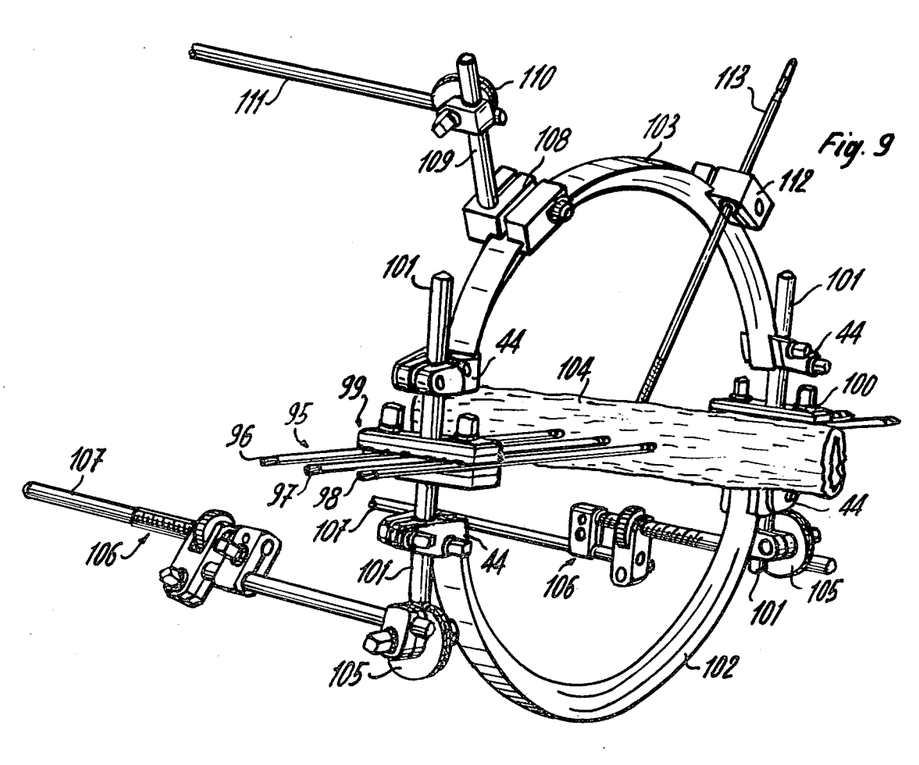
FIG. 9 is a perspective view illustrating the fitting of a part of an external anchoring means, wherein a complete circle, formed by fitting together two semi-circles, is mounted on a group of transfixing pins, and wherein the arrangement carries connecting members for effecting connection with another part, not illustrated, of the external anchoring means.

In the mounting means shown in FIG. 9, illustrating a part of an external anchoring means, a group 95 of three pins 96, 97 and 98 is anchored in two clamps 99 and 100 that are identical to the clamps 17 and 18 used in the embodiment and the variant shown in FIGS. 1 and 2, respectively. Secured on the rods 101, which function like rods 22 and are integral with the jaws of the clamps, are two semi-circles 102 and 103 of triangular cross-section. Assembly pieces, like those described by reference to FIGS. 3 and 4, are used for this securement purpose. The semi-circles 102 and 103 are mounted on the rods 101 in such manner that their peripheries substantially describe a circle, the central axis of which conincides with the axis of a bone fragment 104 held by the group of pins 96 to 98. The lower rods 101 of the clamps 99 and 100 are each provided with a swivel-joint 105 each of which grips a slide bar 106, the free end 107 of which will be solidly connected to the other part, not illustrated in FIG. 9, of the external anchoring means. This other nonillustrated part of the external anchoring means may be similar to the part shown in FIG. 9 or to one of the parts in the FIG. 1 embodiment or the FIG. 2 variant, or it may be similar to one of the variants described hereinafter by reference to FIGS. 10 to 22.

Secured to the arc 103 is a support piece 108, which is identical to the piece 45 shown in FIGS. 7 and 8. The piece 108 grips a rod 109, supporting a swivel-joint 110, and a further rod 111 substantially parallel with the slide bars 106 and performing the same function.

Secured to the semi-circle 103 is a support piece 112 which is identical to the piece 45 shown in FIGS. 7 and 8. In support piece 112 a pin-half 113 is secured. The end of pin half 113 is screwed into the bone fragment 104. The pin-half 113 is introduced into the bore of the support piece 112, having a cylindrical sleeve or lining, not visible in FIG. 9, for the purpose of adapting the undersize diameter of the pin 113 to suit the bore of the corresponding piece 112 which normally corresponds to the diameter of a rod similar to the rods 101, 109, 111, etc.

The presence of the half-pin 113 in the bone fragment 104 enables the arrangement consisting of the bone and the arc to be considerably strengthened. In effect, without the half-pin 113, the transfixing pins 96, 97 and 98 would be able to flex to a quite considerable extent if force were applied in the vertical direction to one of the ends of the bone fragment. The expert will immediately observe that the semi-circles 102 and 103 provide all the space necessary for accommodating other means for positioning additional bone fragments or for increasing the stability of the external anchoring means. On the other hand, since the two semi-circles 102 and 103 completely surround the limb, the bone of which they anchor, this limb is thus enclosed and protected by the anchoring assembly.

Figure 10:
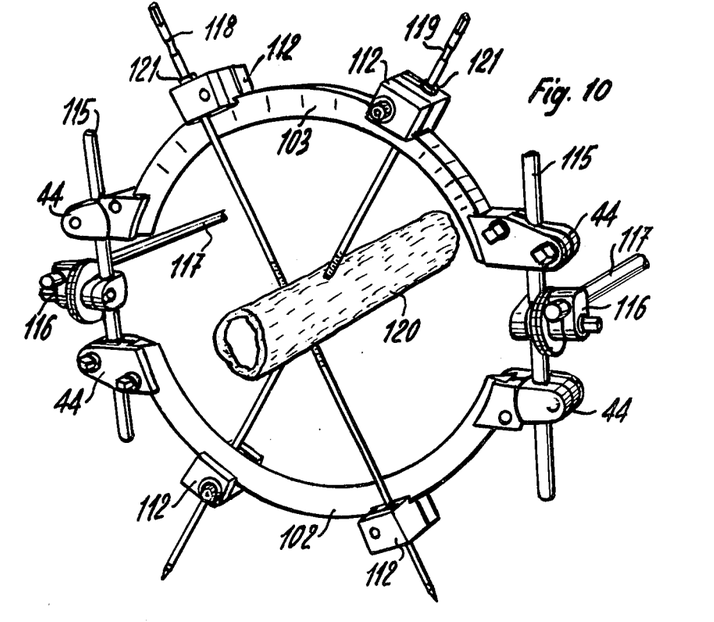
FIG. 10 is a view, likewise in perspective, of a first modified form of the assembly of FIG. 9, wherein the two semi-circles support radial, intersecting, transfixing pins or wires, and wherein each pin or wire is secured by its two ends to the circle.

In the first variant of the FIG. 9 assembly that is illustrated in perspective in FIG. 10, the two semi-circles 102 and 103 are connected at each of their ends by a single rod 115 with the aid of assembly pieces 44. Midway along the rods 115 are located swivel-joints 116 at the ends of rods 117 designed to be secured to the second part, not illustrated, of the external anchoring means. Two transfixing pins 118 and 119 form an angle of approximately 70° between them and they traverse and hold in position a bone fragment 120. The transfixing pins 118 and 119 are held against the semi-circles 102 and 103, respectively, by means of support pieces 112 identical to the corresponding piece 45 shown in FIGS. 7 and 8. In FIG. 10, the sleeves or linings 121 fitted in the bores of the pieces 112 can be seen. The pieces 112 clamp the semi-circles 102 and 103. In FIG. 10, the support pieces 112 are so positioned that the pin 118 extends in front of the two arcs 102 and 103, whereas the pin 118 extends behind them. This method of fitting the pins 118 and 119 renders it possible to avoid crossing the pins in the bone fragment 120. The pins are thus slightly offset from each other. This offsetting, combined with the facts that the pins do not cross each other and are firmly retained over the entire length of the bores in the pieces 112 by means of the sleeves or linings 121, enables the bone fragment 120 to be positioned in a particularly stable manner. It is necessary to apply a very considerble force to one end of the fragment 120 to cause it to shift even slightly.

Figure 11:
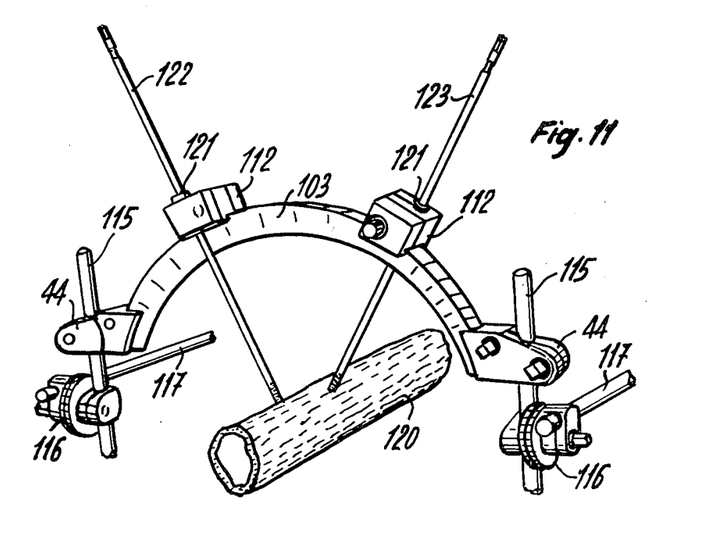
FIG. 11 is a perspective view of a second modified form of the arrangement of FIG. 9, wherein a semi-circle carries two radial pin-halves.

In the second variant of the FIG. 9 embodiment shown in FIG. 11, the bone fragment 120 is held in position by two half-pins 122 and 123 which are not transfixing, that is to say they do not completely pass through the fragment 120. The half-pins 122 and 123 are secured on the semi-circle 103 in the same manner as in the variant shown in FIG. 10, by means of two support pieces 122 and two linings 121. The semi-circle 103 is connected to the external anchoring means, not illustrated, in the same way as in the FIG. 10 variant, with the aid of assembly pieces 44, rods 115, swivel-joints 116 and rods 117.

The embodiments and variants of the assemblies described by reference to FIGS. 9, 10 and 11, i.e. the embodiments wherein a complete circle is formed by two semi-circles, lend themselves particularly to the use of wires instead of pins or half-pins. The wires will be fitted in the same way as the pins, for example, with the aid of the pieces 112 (FIGS. 9 to 11) and sleeves or linings 121 suited to the diameter of the wires. The inventor has developed a turnbuckle, not illustrated, which is applied to the pieces 112 and enables the wires to be tensioned before immobilizing the pieces 112 by means of screws. It is obvious that if wires are used, they must be transfixing, i.e. they must extend completely through the bone or bone fragment. This is the reason why complete circles are particularly well suited for use with wires. The embodiment and variant in FIGS. 1 and 2 also lend themselves to the use of wires. The wires can be tensioned between the two clamps 15, 16 and 17, 18 held in position by the semi-circles 23 and 24. The turnbuckle, not illustrated, is applied to the clamp before immobilizing the screws 21. The wires used will preferably be made of stainless steel.

Figure 12:
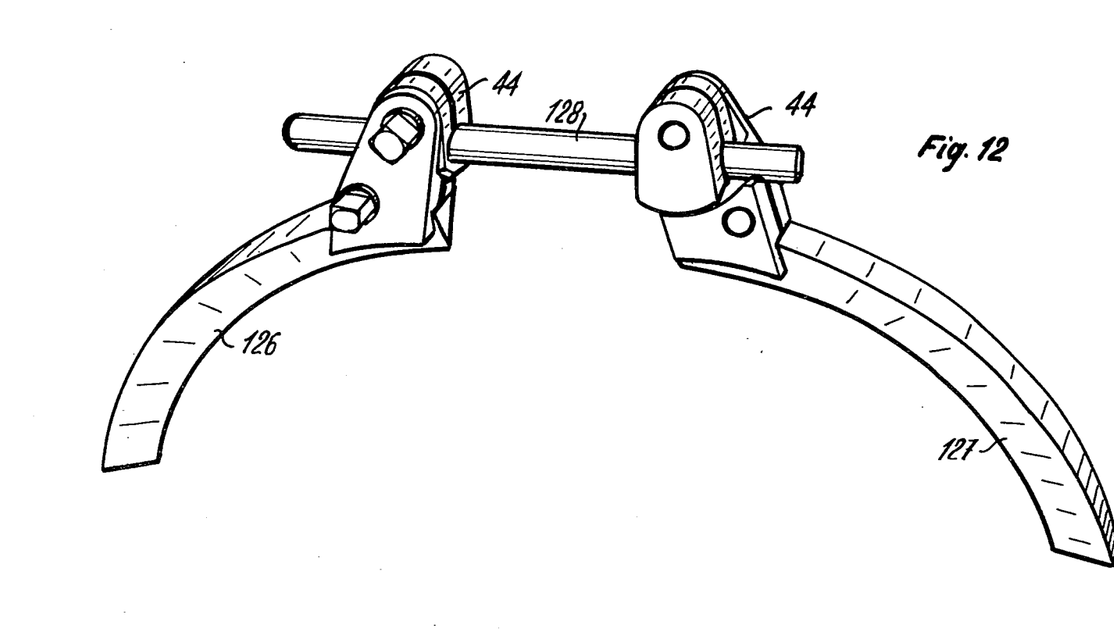
FIG. 12 shows the fitting of two quarter-circles forming a semi-circle.

In the embodiment shown in FIG. 12, a semi-circle is formed from two quarter-circles 126 and 127 held together by two assembly pieces 44 interconnected by a single rod 128. The FIG. 12 embodiment can replace the two semi-circles described in connection with the embodiments and variants of FIGS. 1 to 11. On the rod between the two assembly pieces there can be placed a swivel-joint, not illustrated, for example, which will serve, for instance, for clamping another device for increasing the stability of the external anchoring means on which the two quarter-circles 126 and 127 are fitted, or any device for holding a bone fragment in position. On the other hand, the rod 128 may be replaced by a pin-anchoring clamp, not illustrated, similar to the clamps 15 to 18 used in the previously described arrangements. Each of the quarter-circles 126 and 127 can likewise be provided with any device for holding a bone fragment in position or any means designed to connect the FIG. 12 assembly to a frame of the external anchoring means, not illustrated, of which it forms a part. This can be done with the aid of the support pieces 45 and 51 shown in FIGS. 5 to 8. Finally, the quarter-circles 126 and 127 do not necessarily have to be used together. The fitting of a single quarter-circle where needed can readily be imagined. The quarter-circle 126 would then be provided with two assembly pieces 44 at each of its ends, or with a piece 44 and a support, piece 45 or 51 as in FIGS. 5 to 8, or even simply with support pieces 45 or 51, and the quarter-circle would be connected to an external anchoring means, not illustrated.

Figure 13:
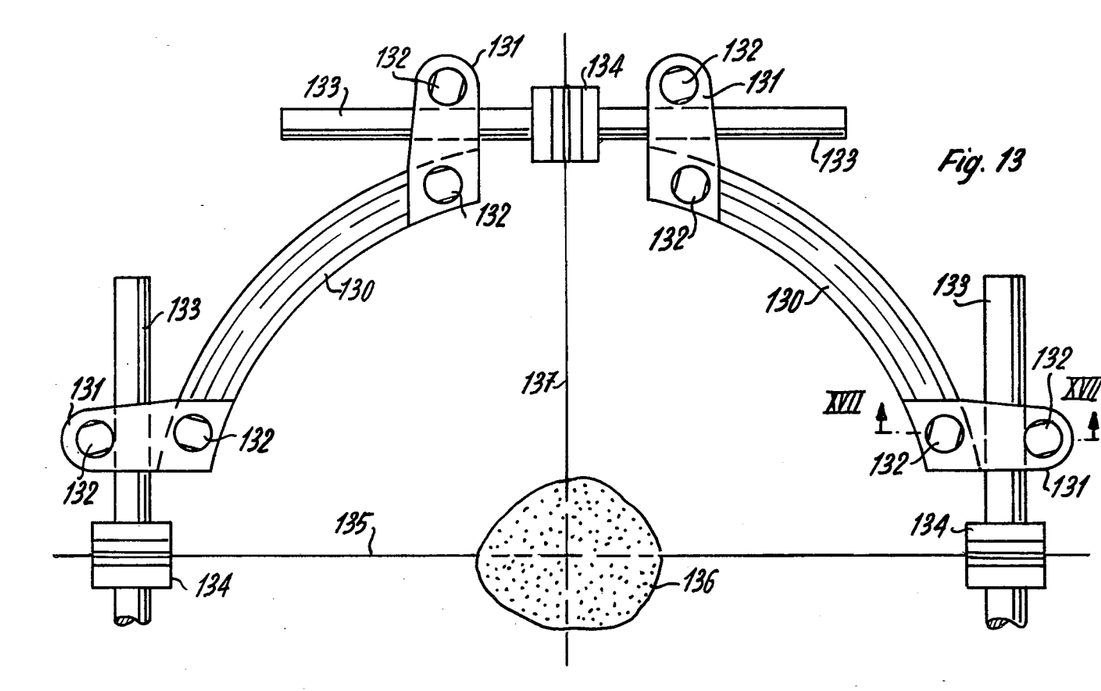
FIG. 13 is a front view of an arrangement comprising two quarter-circles forming a semi-circle, wherein an anchoring device for the pins is held at each end of the two quarter-circles.
Figures 14, 17, 18, 19:
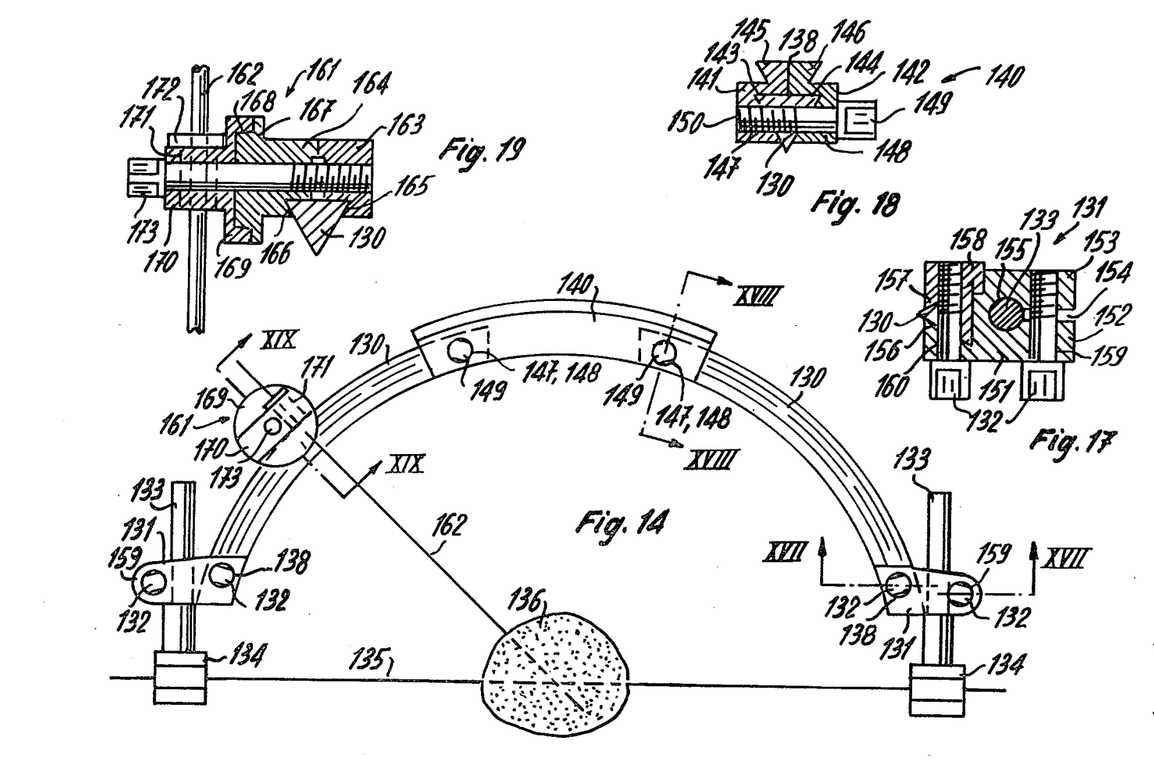

In the FIG. 13 arrangement, two quarter-circles 130 have at their ends assembly pieces 131 illustrated in section in FIG. 17. The assembly pieces 131 make it possible to connect the ends of the arcs 130 very firmly to rods 133 with the aid of screws 132. Each of the rods 133 is connected to a jaw of an anchoring clamp 134 identical to the clamps 15 to 18 in the embodiment and variants shown in FIGS. 1, 2 and 9. The clamps 132 serve to anchor groups of pins 135 and 137, respectively, which hold a bone fragment 136 in position. The quarter-circles 130 are illustrated in detail in FIG. 15 and have at their ends holes 138 into which are passed the screws 132 (FIG. 13) of the assembly pieces 131. The two quarter-circles 130 can clearly be replaced by a semi-circle 139 such as illustrated in FIG. 16. The semi-circle 139 also has at its ends two holes 138 which will enable the screws 132 to be fitted and the assembly pieces 131 to be fixed.

Figure 15:
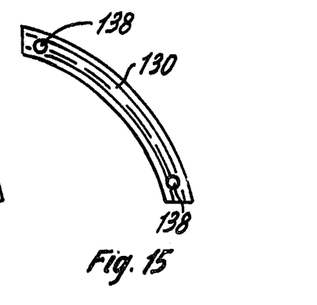
FIG. 15 is a front view of a quarter-circle used in the arrangements shown in FIGS. 13 and 14.
Figure 16:
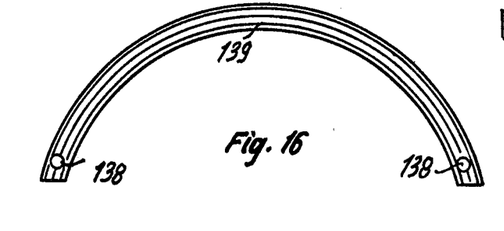
FIG. 16 illustrates a front view of a semi-circle adapted to replace the quarter-circles, for example, as well as the intermediate assembly piece of FIG. 14.

In the FIG. 14 arrangement which represents a variant of the FIG. 13 arrangement, two quarter-circles 130 identical to those of FIG. 13 and consequently to the quarter-circles illustrated in FIG. 15 are provided at their opposite ends with assembly pieces 131 screwed on to the ends of the arcs 130 with the aid of screws 132. The assembly pieces 131 are in turn fitted on rods 133 of the upper jaws of the anchoring clamps 134. Firmly held in the two clamps 134 is a group of transfixing pins 135 which hold a bone fragment 136 in position.

The two quarter-circles 130 are interconnected by a central piece 140 shown in section in FIG. 18. Referring to the section in FIG. 18, it can be seen that the intermediate piece 140 comprises two parts 141 and 142 having interior grooves 143 and 144, respectively, enabling the triangular ends of the arcs 130 to be gripped. It can be seen from FIG. 14 that the piece 140 has the same curvature as the arcs 130. On the other hand, the parts 141 and 142 of the piece 140 have two ribs 145 and 146 along their outer periphery, which ribs together form a triangular cross-section which will permit of the securing, to the piece 140, of the support pieces 45 illustrated in FIGS. 7 and 8, or the support pieces 51 illustrated in FIGS. 5 and 6, or the modified forms of these pieces, for example, the variant illustrated in FIG. 19 which will be described later. The parts 141 and 142 each have a bore 147 and 148 which bores are in alignment and which will permit the introduction of a screw 149 designed to immobilize the two parts 141 and 142 of the piece 140. It will be seen in FIGS. 14 and 18, that the screw-threaded part 150 of the screw 149 meshes with a complementary screw-threaded portion in the bore 147 after having passed through the bore 138 at the end of the arc 130. With the screw 149 immobilized, the arcs 130 are retained in a stable and firm manner in the piece 140.

The advantage of the arrangement shown in FIG. 14 and comprising two quarter-circles 130 and the piece 140 resides in the fact that the support pieces, similar to those illustrated in FIGS. 5 to 8, can be fitted at any selected position along the entire periphery of the arc, including the back of the piece 140. The pieces 140 are of different lengths such that with the quarter-circles 130 they are able to form semi-circles of different diameter. Thus, the FIG. 14 arrangement offers an extended range of uses of the quarter-circles 130.

FIG. 17 illustrates in section the assembly pieces 131 which enables the ends of the arcs 130 to be fitted to the rods 133 in the FIGS. 13 and 14 arrangements. The assembly piece 131 comprises a clamp 151, one end of which has two side-faces 152 and 153 separated by a groove 154 and forming at the middle a bore 155 intended to accommodate the rod 133. The other end of the clamp 151 comprises a groove 156 intended to grip the triangular cross-section of the quarter-circle 130 by cooperating with a further corresponding groove 157 formed in a cooperating clamp 158. Two bores 159 and 160 are formed in the two ends of the piece 151 as well as in the piece 158. The bore of the piece 158 is screw-threaded, as is the bore associated with the side-face 153 of the piece 151, and these two bores are designed to accommodate the screw-threaded parts of the screws 132. Examination of FIG. 17 will immediately show that the tightening of the two screws 132 will cause immobilization of the rod 133 on the one hand, and immobilization of the quarter-circle 130 between the pieces 151 and 158, the screw 132 extending through the bore 138 of the quarter-circle 130.

Secured to the quarter-circle 130 located to the left in the FIG. 14 arrangement is a support clamp 161 provided with a swivel-joint and designed to position a rod 162 used for reinforcing the anchorage of the bone fragment 136 achieved with the aid of a group of pins 135. The support piece 161 illustrated in section in FIG. 19 comprises two parts 163 and 164 having grooves 165 and 166, respectively, designed to grip the triangular cross-section of the quarter-circle 130. The part 164 has a small circular collar 167 terminating in a frusto-conical portion 168. The collar 167 and the frusto-conical portion 168 cooperate with a complementary female piece 169 on which is mounted an extension 170. Formed in the extension 170 is a bore 171 in which is provided a lining or sleeve 172 designed to match the diameter of the pin 162 to that of the bore. The entire piece 161, i.e. the parts 163 and 164, the collar 167 and its frusto-conical extension 168, and the corresponding piece 169 as well as the lining 167, can be immobilized by a single screw 173. The frusto-conical part 168 as well as the corresponding female part of the piece 169 forms an angle of a few degrees so that the swivel-joint formed by the pieces 167, 168 and 169 is completely immobilized when the screw 178 is tightened to secure the piece on the quarter-circle 130. The particular purpose of the piece 161 resides in the fact that the pin 162 which it carries can be turned about the axis of the screw. It is thus possible to position the pin 162 in the bone-fragment 136 precisely at the place required.

Figure 20:
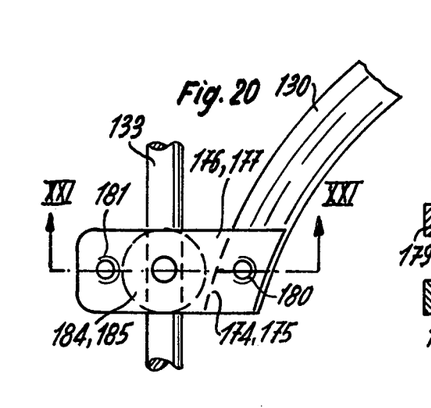
FIG. 20 is a front view of a modified form of the end piece of the semi-circles of FIGS. 13, 14 and 17.
Figure 21:
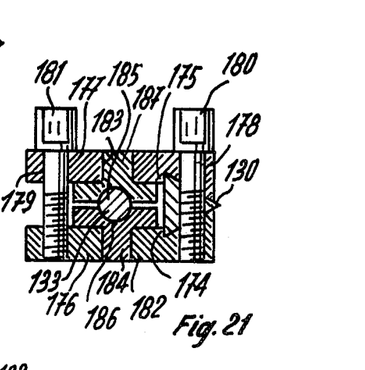
FIG. 21 is a view along line XXI—XXI of FIG. 20.

FIGS. 20 and 21 illustrate a modified form of the assembly piece 131 used in the arrangement illustrated in FIGS. 13 to 19. It has been seen that the piece 131 enables the rods 133 (see FIGS. 13 and 14) to be gripped only in one direction, that is to say that with these pieces 131 the arcs in the arrangements shown in FIGS. 13 and 14 can only be fitted in a symmetrical manner. In the case where it is desired to position the arcs 130 of FIGS. 13 and 14 in such a way that, for example, the ends of the arcs are located at a higher level on one of the rods 33 than on the other rod, it is necessary to provide a further assembly piece. For this purpose, the assembly piece illustrated in FIGS. 20 and 21 is provided. Referring to these two Figures, the arc 130 is gripped in the grooves 174 and 175 of the clamps 176 and 177, respectively. The clamps 176 and 177 have a bore 178 and 179 at each of their ends. These bores are intended to receive screws 180 and 181. At their middle, the pieces 176 and 177 have bores 182 and 183 into which are introduced circular pieces 184 and 185. On their adjacent surfaces, the circular pieces 184 and 185 have two corresponding grooves 186 and 187 adapted to grip the rod 133. It can be clearly seen from FIGS. 20 and 21 that immobilization of the screws 180 and 181 causes the clamps 176 and 177 to be pressed against the quarter-circle 130 on the one hand, and compresses the rod 133 by way of the circular pieces 184 and 185, on the other hand. The modified form of the assembly piece shown in FIGS. 20 and 21 enables the assembly consisting of the piece and the quarter-circle 130 to be pivoted about the rod 133, or vice versa.

Figure 22:
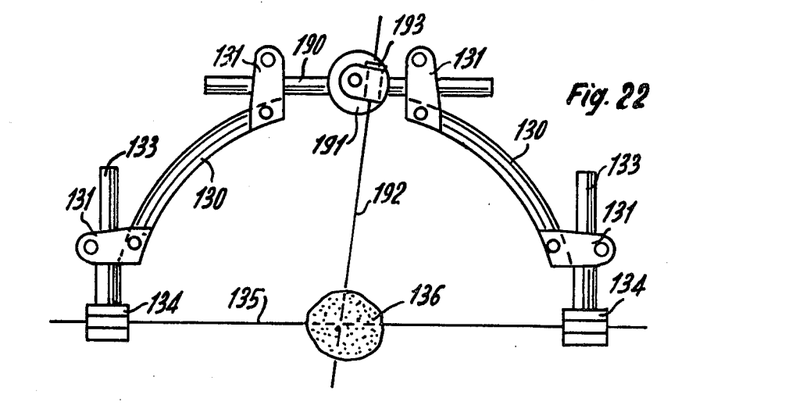
FIG. 22 is a front view of a modified form of the FIG. 14 arrangement.

In the arrangement shown in FIG. 22, the quarter-circles 130 are secured to the rods 133 of the clamps 134 by way of assembly pieces 131 as illustrated in FIG. 17, or variants of these pieces shown in FIGS. 20 and 21. The clamps 134 serve to retain a group of transfixing pins 135 which hold a bone fragment 136 in position. At their upper ends the quarter-circles 130 are connected to a rod 190 by way of two assembly pieces 131. Mounted on the rod is a swivel-joint 191 similar to the toothed swivel-joint 61 shown in the embodiment and variant illustrated in FIGS. 1 and 2. Secured in the bore of the toothed swivel-joint 191 is a pin 192 enclosed in a liner 193 which is designed to adapt the diameter of the pin 192 to suit the diameter of the bore in the swivel-joint 191. As in the arrangement shown in FIGS. 13 and 14, the FIG. 22 arrangement enables a bone fragment 136 to be held more firmly in position by means of an additional pin 192. Since the swivel-joint is able to turn about the rod 192 in either direction, it can also be used for maintaining a further bone fragment adjacent the fragment 136.

Figure 23:
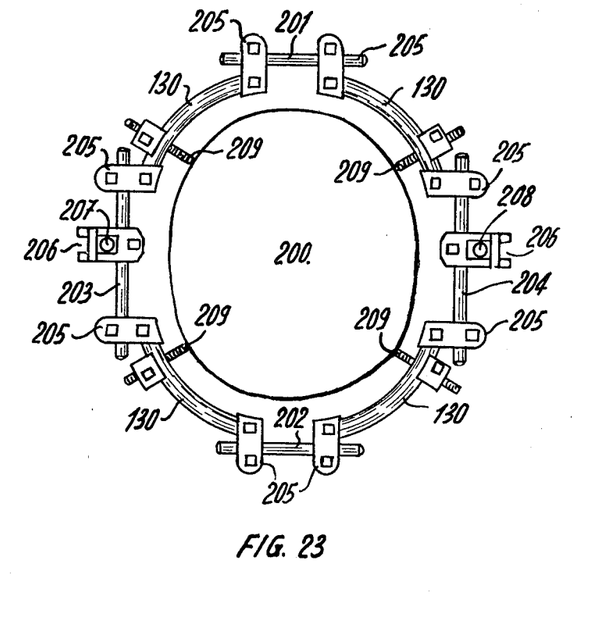
FIG. 23 is a plan view of an arrangement made up of four quarter-circles arranged to form a ring for holding a patient's head in position.
Figure 24:
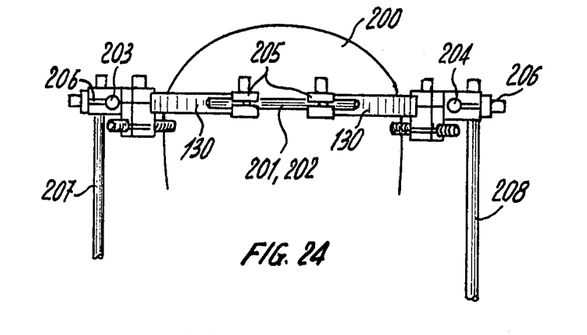
FIG. 24 is a side view of the arrangement illustrated in FIG. 23.

In the fitting of the halo illustrated in FIGS. 23 and 24, the surround for the head 200 of the patient is formed by four quarter-circles 130 which are identical to those illustrated in FIG. 13 and the ends of which are connected to bars 201, 202 and 203, 204, respectively, by means of clamping pieces 205 illustrated in FIGS. 3 and 4, and 17 or 21. Mounted on the bars 203 and 204 are swivel-joint assembly pieces 206 which hold the rods 207 and 208 perpendicular to the plane of the halo formed by the assembly comprising the four quarter-circles 130. The rods 207 and 208 will be secured to a jacket, not illustrated, worn by the patient, by way of a fitting consisting of bars or rods, likewise not illustrated, or by means of a fitting directly secured to the clavicles or shoulder-blades of the patient with the aid of transcutaneous pins. The head 200 of the patient will be held within the halo formed by the quarter-circles 130 by means of pointed screws 209. The point of each screw 209 bears on the cranial bones of the patient. The screws 209 are held perpendicular to the quarter-circles 130 by means of the assembly pieces 45 shown in FIG. 7 into which will have been fitted a sleeve or lining similar to the lining 121 shown in FIGS. 10 and 11. The bore of the lining 121 has a screw-thread corresponding to the screw-thread of the pointed screws 209.

The above-described halo supports the weight of the head 200 of the patient and prevents any movement of the head. It is used, for example, in the treatment of lesions of the cervical vertebrae, or in the treatment of arthritis or scoliosis.

An arrangement similar to that just described for forming the halo may also be used for the treatment of lesions of the pelvis or lumbar vertebrae. In this case, the system will not necessarily be a closed one as in the case in the arrangement shown in FIGS. 23 and 24. It can be formed from two or three quarter-circles connected to a frame comprised of rods and an assembly member. The system and/or the frame will be secured to the iliac bone and/or to the sacro-iliac bone by means of transcutaneous pins. It is possible for the frame mounts to be formed with the aid of arcuate parts extending from the pelvis to the head by securing the system on the iliac bones, the shoulder-blades and the clavicles with the aid of transcutaneous pins in the case of lesions extending over the entire length of the vertebral column.

In the embodiments and variants that have been described, the anchoring means comprise either complete circles formed from two semi-circles, or semi-circles formed from quarter-circles with intermediate pieces. It is clear that a complete circle is also envisaged, which is of triangular cross-section and which would be used in conjunction with the assembly pieces or the support pieces. The main advantages of the embodiments that have been described are as follows:

The external anchoring means can be fitted either with the aid of a semi-circle which can be in one piece or constituted by two quarter-circles, and intermediate pieces, or a complete circle which can be in one piece or formed by two semi-circles. Thus, generally a semi-circle or a complete circle will be fitted for each bone to be held in position, each semi-circle or complete circle forming what is called a frame. The two frames will then be held in position by a connecting means which may be comprised either of slide bars or single assembly rods. The slide bars offer the advantage of enabling the distance between two frames to be altered, i.e. the distance between two semi-circles or complete circles each holding a bone fragment in position. In a modified form, not illustrated, it is possible to mount the two frames with the aid of the clamps 15 to 18, shown in FIG. 1, and their transfixing pins. The clamps are held in position by means of slide bars or connecting rods. A single arcuate element is fitted where it is necessary and useful. Such an arrangement can be envisaged in the case illustrated in the FIG. 2 variant where only the arc 23 can be considered as being of use in view of the fact that it enables the further bone fragment 50 to be held in position with the aid of the rod 52, the clamp 53 and the pins 54 and 55. This arrangement, comprising only one part-circle, can be advantageously used for example for an anchoring means which is to retain bone fragments on, for example, the pelvis or the clavicle of a human body.

In all the embodiments described, the connecting means is an existing one, and it can be used in combination with the arcuate parts. This means consists of the rods, the slide bars, the anchoring clamps, the swivel-joints, etc.

The external bone-anchoring elements that have been described by reference to FIGS. 1 to 22 offer the following advances over existing systems:

1. Conventional frames formed by clamps, pins and connecting bars joined by the conventional means, in particular slide-bars and rods, can be used in combination with arcuate parts.
2. The fixing means enable pins or groups of pins to be located in any plane by virtue of the arrangement of the arcs which serve as fixing means for pins which may extend laterally of them.
3. The fixing means enable the arcs to be adjusted vertically in relation to soft parts.
4. The fixing means offer the possibility of securing, either on the arc or on the rods, complementary fixing means which may be transfixing or otherwise and which are located in another plane.

5. There is a possibility of providing a complete circle either comprised of a single piece or of semi-circles or quarter-circles.

6. There is a possibility of connecting the arcs or circles independently of each other, or one to the other, by means of rigid bars or slide-bars permitting adjustment of the distance between the fragments and enabling the mounting means obtained to be rendered more solid.

7. There is a possibility of using the "Russian" technique, which requires complete circles for the treatment of body extremities.

The parts forming the external anchoring means that have been described will preferably be made of a stainless or non-corroding metal, particularly the pins, wires, swivel-joints, anchoring clamps, rods, slide bars, etc. On the other hand, the circles or arcs, as well as the assembly and support pieces designed to be secured to the circles or arcs, can be made of a light alloy particularly one based on aluminum or titanium. The pins which extend through the soft portions of the body as well as the bone are electrically insulated from each other and from the other parts of the anchoring means.

The advantages of the anchoring means described above are as follows:

(1) The apparatus can be assembled either with one or two arcs for each bone fragment. It suffices to provide between the two arcs a connecting rod which, depending upon its length, can alter the distance between the two arcs and can therefore be used in a large number of cases with the same size of arc.

(2) The connecting device is an existing device, i.e. either a Hoffman swivel-joint with a slide bar, or an immobilizing unit forming the subject matter of Swiss Pat. No. 579,438 and now commercially available for very small anchoring devices.

Although a preferred embodiment of this invention has been described, many variations and modifications will now be apparent to those skilled in the art, and it is therefore preferred that the instant invention be limited not by the specific disclosure herein, but only by the appending claims.

What is claimed is:

1. An external bone-anchoring means, comprising two groups of pins, each group being comprised of at least one pin, or the like, for retaining a bone portion, at least one assembly rod for interconnecting the two groups, and at least one arcuate member of polygonal cross-section connected to the assembly rod adjacent one of the groups of pins, the arcuate member having no discontinuities over its length and having a uniform cross-section over its length for enabling the assembly rod to be connected to the arcuate member anywhere along its length.

2. An external bone-anchoring means according to claim 1 wherein the assembly rod is interconnected to one of the groups of pins by at least one support piece, the support piece is removably secured to the arcuate member and is for supporting at least one pin or the like, which retains at least one piece of bone.

3. An external bone-anchoring means according to claim 1 wherein the support piece comprises jaws having internal recesses adapted to complement at least a portion of the polygonal cross-section of the arcuate member so as to be capable of being pressed onto and immobilized on the arcuate member without being able to rotate about it or move along it.

4. An external bone-anchoring means according to claim 3, wherein the support piece has a bore therein into which may be introduced a pin or the like.

5. An external bone-anchoring means according to claim 4 wherein the bore is provided with a sleeve lining therein with an opening adapted to match the diameter of the pin, or the like.

6. An external bore-anchoring means according to claim 4 wherein the bore is so disposed in the piece that the axis of the bore extends radially of the arcuate member when the piece is secured to the arcuate member.

7. An external bone-anchoring means according to claim 6 wherein the bore is provided with a sleeve lining therein with an opening adapted to match the diameter of the pin or the like.

8. An external bone-anchoring means according to claim 4 wherein the bore is so disposed in the piece that the axis of the bore is perpendicular to the plane of the arcuate member when the piece is secured to the arcuate member.

9. An external bone-anchoring means according to claim 8 wherein the bore is provided with a sleeve lining therein with an opening adapted to match the diameter of the pin or the like, the bore is extended into two portions of the piece located at each side of the arcuate member, and the pin or the like with the lining being retained by flexion in the bore when the two parts are immobilized against the arcuate member.

10. An external bone-anchoring means according to claim 3 wherein the support piece has a first portion secured to the arcuate member by a clamping screw and has a second, pivoting portion which pivots about the clamping screw and relatively to the support piece as a whole, the support piece pivoting portion having a bore formed therein into which may be introduced a pin or the like.

11. An external bone-anchoring means according to claim 10 wherein the pivoting portion is comprised of two clamps having adjacent interior surfaces which each contain a recess, and the two recesses define the bore.

12. An according to claim 2 wherein the support piece has a bore therein into which may be introduced a pin or the like, the assembly piece has two circular portions mounted to rotate and to engage by friction in the piece as a whole, the adjacent surfaces of the circular portions having corresponding recesses defining the bore.

13. An external bone-anchoring means according to claim 2 wherein the support piece has a bore therein into which may be introduced a pin or the like, a swivel-joint adapted to permit immobilization in the required position and being mounted on the support piece, the bore being present in the swiveling part of the joint and the axis of the bore being perpendicular to the swivel axis of the joint.

14. An external bone-anchoring means according to claim 2 wherein the arcuate member is comprised of at least one section thereof which is a quarter of a circle.

15. An external bone-anchoring means according to claim 2 wherein the arcuate member is comprised of at least one section thereof which is a semi-circle.

16. An external bone-anchoring means according to claim 2 wherein the arcuate member is comprised of at least one section thereof which is of the arcuate length of part of a circle.

17. An external bone-anchoring means according to any one of claims 14, 15, or 16 wherein the arcuate member is comprised of two of the sections thereof which respectively are interconnected by an intermediate piece of sutstantially the same curvature as the arcuate member sections, the outer periphery of the intermediate piece having, at least in part, the same profile as the sections, so that the support piece may also be secured to the intermediate piece.

18. An external bone-anchoring means according to claim 17 wherein the ends of the section have holes into which screws may extend for connection to an adjacent one of the sections and the intermediate piece.

19. An external bone-anchoring means according to any one of claims 14, 15 or 16 wherein the ends of the section have holes into which screws may extend for connection to an adjacent one of the sections.

20. An external bone-anchoring means according to claim 2 wherein the arcuate member is comprised of a complete circle.

21. An external bone-anchoring means according to claim 2 wherein the arcuate member is comprised of at least one section thereof which is of the arcuate length of part of a circle; the arcuate member is comprised of two of the sections thereof which respectively are interconnected by an intermediate piece of substantially the same curvature as the arcuate member sections, the outer periphery of the intermediate piece having, at least in part, the same profile as the sections, so that the support pieces may also be secured to the intermediate piece.

22. An external bone-anchoring means according to claim 2 wherein the arcuate member has a triangular cross-section.

23. An element according to claim 2 further comprising a swivel joint secured on the arcuate member and the support piece being held to the swivel joint and swivelable therewith, a pin or the like being supported by the swivel joint and extending to the bone for engaging it, and the swivel joint enabling the angle at which the pin, or the like, extends toward the bone to be adjusted.

24. An element according to claim 23 wherein the swivel joint is adapted to swivel around an axis generally parallel to the axis of the arcuate member.

25. An element according to either of claims 23 or 24 wherein the swivel joint is adapted to swivel around an axis generally tangent to the axis of the arcuate member.

26. An element according to claim 23, wherein the arcuate member is comprised of two arcuate segments which are secured together and a swivel joint is connected between the arcuate segments.

27. An external bone-anchoring means according to claim 1, further comprising a respective clamping device for anchoring each end of the pins of at least one group of pins, the arcuate member is connected to the two clamping devices for the one group of pins.

28. An external bone-anchoring means according to claim 1, wherein the arcuate member is semicircular, and the pins of at least one group of pins are secured in a cruciform arrangement to the semi-circular arcuate member.

29. An external bone-anchoring means according to claim 1 further comprising additional pins for retaining additional bone fragments, the pins being secured to the arcuate member, and devices for positioning the additional fragments laterally in relation to the arcuate member.

30. An external bone-anchoring means according to claim 1, further comprising at least two of the arcuate members, one respectively for each of the groups of pins, the assembly rod interconnecting the arcuate members.

31. An external bone-anchoring means according to claim 10, wherein the two arcuate members each have respective support pieces, an additional support piece being positioned on one of the arcuate members, additional pins and a pin support on the additional support piece, the pin support being for supporting the additional pins, such that the additional pins extend toward a bone piece that is located between the bone pieces respectively engaged by the pins or the like supported by the support pieces on the two arcuate members.

32. An external bone-anchoring means according to claim 31, wherein the additional support piece includes a rod extending from the respective arcuate member to a location between the two arcuate members at the pin supports carried on the rod.

33. An external bone anchoring means according to claim 30, wherein each arcuate member also supports a respective support piece along the arcuate length of the respective arcuate member, a respective support piece on each arcuate member being paired with a support piece on the other arcuate member, the pins, or the like, extend between the respective paired support pieces for transfixing a bone.

34. An external bone anchoring means according to claim 33, wherein the paired support pieces include aligned bores for receiving the respective pins or the like in them.

35. An external bone-anchoring means according to claim 34, wherein the pins or the like are threaded along their portion which transfixes a bone.

36. An external bone-anchoring means according to claim 33, wherein the support piece is held to the arcuate member and includes a swivel joint therein which is adapted to swivel around an axis generally parallel to the axis of the arcuate member, a pin or the like held by the additional support piece to be swiveled therewith.

37. An external bone-anchoring means according to claim 36 wherein the pins or the like are threaded along their portion which enters the bone.

38. An external bone-anchoring means according to claim 1 wherein the arcuate member is comprised of two sections thereof each of which is of the arcuate length of part of a circle; the arcuate member sections being interconnected by an intermediate piece of substantially the same curvature as the arcuate member sections, the outer periphery of the intermediate piece having, at least in part, the same profile as the sections, so that the pieces may also be secured to the intermediate piece.

39. An external bone anchoring means according to claim 27, in which a complete arcuate member comprises two support pieces fixed on the member by means of respective jaws of the support pieces and further comprises at least a wire tightened up between the two support pieces.

* * * * *